United States Patent [19]

Beedle et al.

[11] Patent Number: 4,632,939
[45] Date of Patent: Dec. 30, 1986

[54] ANTICONVULSANT AGENTS

[75] Inventors: Edward E. Beedle; David W. Robertson, both of Indianapolis, Ind.

[73] Assignee: Eli Lilly and Company, Indianapolis, Ind.

[21] Appl. No.: 711,929

[22] Filed: Mar. 15, 1985

[51] Int. Cl.⁴ .................. A61K 31/165; C07C 103/28
[52] U.S. Cl. ..................................... 514/619; 564/166; 564/168
[58] Field of Search ................ 564/166, 168; 514/619; 534/841, 659, 860

[56] References Cited

U.S. PATENT DOCUMENTS

| | | | |
|---|---|---|---|
| 2,034,054 | 3/1938 | Morschel | 534/841 X |
| 2,551,570 | 5/1951 | von Glahn et al. | 564/168 X |
| 3,494,911 | 2/1970 | de Montmollin | 534/860 |
| 4,004,029 | 1/1977 | Collins et al. | 514/619 |
| 4,049,717 | 9/1977 | Asato | 564/166 X |
| 4,379,165 | 4/1983 | Clark | 424/324 |
| 4,511,581 | 4/1985 | Ohsumi et al. | 564/166 X |

OTHER PUBLICATIONS

Forbes et al., Journal Chem. Soc. 1963, 835–839.
Seidl et al., Tetrahedron, 1964, vol. 20, pp. 633–640.
Petyunin et al., Zhurnal Obshchei Khimii, 1960, vol. 30, pp. 2028–2030.

Primary Examiner—Charles F. Warren
Assistant Examiner—Carolyn S. Greason
Attorney, Agent, or Firm—Robert A. Conrad; Arthur R. Whale

[57] ABSTRACT

This invention provides certain benzamide derivatives of the formula:

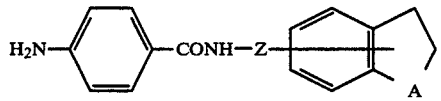

wherein
Z is bond, —CH$_2$—, or CHCH$_3$; A is —CH$_2$—, or CH$_2$CH$_2$—; and represents a single or double bond; and their pharmaceutical formulations and their use as anticonvulsant agents.

13 Claims, No Drawings

ANTICONVULSANT AGENTS

BACKGROUND OF THE INVENTION

The several anticonvulsant drugs marketed in the United States provide significant seizure relief for only 50-75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See "The Pharmacological Basis of Therapeutics" (Gilman, Goodman, and Gilman, ed., 6th Ed., MacMillan Publishing Co., Inc., New York, N.Y. (1980)), p. 455. In view of these facts, most epileptologists indicate there is a definite need for more selective and less toxic anticonvulsant drugs.

SUMMARY OF THE INVENTION

This invention provides p-aminobenzamides of the formula I

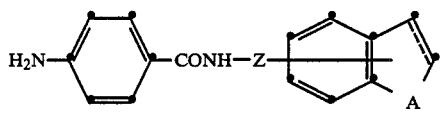

wherein
Z is a bond, $-CH_2-$, or $-CHCH_3-$;
A is $-CH_2-$, $-CH=CH-$, or $-CH_2CH_2-$; and
---- represents a single or double bond;
and
pharmaceutically acceptable acid addition salts thereof.

This invention also provides a method for treating and preventing convulsions in mammals in need of such treatment which comprises administering to said mammal an effective amount of a compound as defined above.

According to a further aspect of the present invention, there are provided pharmaceutical formulations which comprise as active ingredient a benzamide of formula I in association with a pharmaceutically acceptable carrier or diluent.

This invention also provides compounds of the formula II

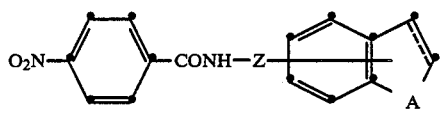

wherein
Z and A are the same as previously defined. These nitro derivatives are useful as intermediates for preparing the anticonvulsant p-aminobenzamides of formula I.

DETAILED DESCRIPTION AND PREFERRED EMBODIMENT

The present invention relates to organic compounds that are useful for treating and preventing convulsions in mammals.

In the structure of formula I, the aminobenzamido-substituted Z functionality may be attached at any position of the bicyclic system. It is preferred that Z is a bond. It is also preferred that the bicyclic system is substituted at a carbon atom adjacent to the bridgehead. When Z is $-CHCH_3-$, two optically active isomers of the compounds of formula I are possible. This invention includes both the individual enantiomers as well as the racemate of such compounds.

The pharmaceutically acceptable acid addition salts of this invention can be prepared by standard methods known in the art employing those acids of sufficient acidity to form acid addition salts with the basic aniline group. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxyalkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1-sulfonate, naphthalene-2-sulfonate and the like. Preferred salts are those derived from inorganic acids, especially hydrochloric acid.

The compounds of formula I may be prepared by any of several methods well known in the art. A preferred method comprises reacting a p-nitrobenzoyl halide III with an amine IV according to the general method as taught in U.S. Pat. No. 4,379,165, and according to the following scheme:

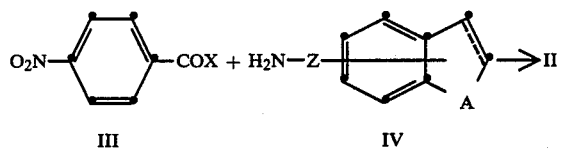

wherein
X is a leaving group such as $C_1-C_3$ alkoxy or halo, especially chloro, and Z and A are the same as previously defined. The reaction follows the general procedure of reaction A in the above mentioned patent. It is preferred that a benzoyl halide and the amine be reacted in a non-reactive solvent, such as tetrahydrofuran, preferably in the presence of an acid scavenger such as a carbonate, especially potassium carbonate, or an organic base, such as triethylamine. Although it is preferred that the reactants be added in molar ratios of about 1.5:1.0 (III:IV), other ratios are completely operative. The reaction is carried out from about room temperature up to the reflux temperature of the reaction mixture. Under the preferred conditions of reflux, the reaction is generally complete in 1-12 hours.

The p-nitrobenzamides of the invention may be converted into the corresponding p-aminobenzamides by any of a number of reductive methods. The preferred procedure is the hydrogenation procedure which may be identical with or equivalent to the conditions taught as reaction B in the above patent. Generally, the p-nitrobenzamide is hydrogenated under low pressure in a nonreactive solvent such as an alcohol, especially ethanol, in the presence of a catalyst, such as palladium on charcoal. The reaction is generally complete in about 2-4 hours.

The individual enantiomers of this invention may be prepared from the racemate (i.e., when Z is —CHCH$_3$—) by standard methods of isomeric resolution known in the art, such as crystallization, salt formation, high pressure liquid chromatography, etc. In addition, the enantiomers can be prepared by resolving the intermediate p-nitrobenzamide in the same manner and then hydrogenating the individual isomers in the usual way. However, the preferred method of preparing the enantiomers of this invention comprises reacting a p-nitrobenzoyl halide with enantiomerically pure amine followed by reduction.

Alternatively, the p-nitrobenzamide intermediates of formula II may be prepared, for example, from p-nitrobenzoic acid ester derivatives of III (e.g., where X is OCH$_3$) upon reaction with IV. This aminolysis reaction is generally known and is preferably accomplished by heating the two reactants in a non-reactive solvent such as an alcohol, at temperatures from about 40°-100° C. Anhydrides of p-nitrobenzoic acid may also be employed in the reaction with the amines of Formula IV. In addition, p-nitrobenzoic acid may be reacted with the required amine in the presence of coupling reagents such as DCC, EEDQ, CDI, etc.

The intermediates of Formulas III and IV and other necessary reagents are commercially available, are known in the art, or can be prepared by methods taught in the literature.

The p-aminobenzamides of this invention are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. The invention includes a pharmaceutical composition comprising from about 1% to about 95% by weight of a p-aminobenzamide of Formula I or a pharmaceutically acceptable acid addition salt thereof associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples further illustrate the preparation of the intermediates, compounds, and formulations of this invention. The examples are illustrative only and are not intended to limit the scope of the invention in any way.

EXAMPLE 1

4-Nitro-N-(1,2,3,4-tetrahydro-1-naphthalenyl)-benzamide

A solution of 18.9 g of 4-nitrobenzoyl chloride in 100 ml of tetrahydrofuran was added rapidly to a solution of 10.0 g of 1,2,3,4-tetrahydro-1-naphthylamine in 200 ml of tetrahydrofuran and 180 ml of 20% aqueous potassium carbonate. The reaction mixture was stirred vigorously and heated at reflux for 2 hours. After cooling, the layers were separated and the aqueous layer was extracted with ethyl acetate. The combined organic portions were washed with water, 1N hydrochloric acid, water, and a saturated sodium chloride solution, dried over sodium sulfate, and concentrated in vacuo. The resulting solid was recrystallized from benzene to afford the title intermediate in 90% yield as a colorless solid, m.p. 156°-157° C.

Analysis for $C_{17}H_{16}N_2O_3$: Calculated: C, 68.91; H, 5.44; N, 9.45; Found: C, 68.74; H, 5.34; N, 9.43.

EXAMPLES 2-6

The following p-nitrobenzamides were prepared according to the procedure of Example 1 employing the appropriate amine derivative.

2. N-(2,3-dihydro-1H-inden-1-yl)-4-nitrobenzamide, 82% yield, m.p. 164°-166° C.

Analysis for $C_{16}H_{14}N_2O_3$: Calculated: C, 68.08; H, 5.00; N, 9.92; Found: C, 68.28; H, 4.78; N, 9.65.

3. (S)-N-[1-(1-naphthalenyl)ethyl]-4-nitrobenzamide, 80% yield, m.p. 156°-157° C.

Analysis for $C_{19}H_{16}N_2O_3$: Calculated: C, 71.24; H, 5.03; N, 8.74; Found: C, 69.33; H, 5.05; N, 8.47.

4. 4-Nitro-N-(5,6,7,8-tetrahydro-1-naphthalenyl)benzamide, 73% yield, m.p. 204°-205° C.

Analysis for $C_{17}H_{16}N_2O_3$: Calculated: C, 68.91; H, 5.44; N, 9.45; Found: C, 68.69; H, 5.55; N, 9.31.

5. N-1-naphthalenyl-4-nitrobenzamide, 68% yield, m.p. 200°–201.5° C.

Analysis for $C_{17}H_{12}N_2O_3$: Calculated: C, 69.86; H, 4.14; N, 9.58; Found: C, 69.57; H, 4.36; N, 9.36.

6. N-2-naphthalenyl-4-nitrobenzamide, 73% yield, m.p. 204°–206° C.

Analysis for $C_{17}H_{12}N_2O_3$: Calculated: C, 69.86; H, 4.14; N, 9.58; Found: C, 69.75; H, 3.88; N, 9.45.

EXAMPLE 7

4-amino-N-(1,2,3,4-tetrahydro-1-naphthalenyl)benzamide hydrochloride

A solution of 7.5 g of 4-nitro-N-(1,2,3,4-tetrahydro-1-naphthalenyl)benzamide from Example 1 in 200 ml of ethanol was hydrogenated over 5% palladium on carbon until the theoretical amount of hydrogen was consumed. The catalyst was removed by filtration and the filtrate was concentrated in vacuo. The resulting solid was chromatographed over silica gel to afford the title product (base) as an oil in 87% yield. The hydrochloride salt was generated in ethanol with a stoichiometric amount of hydrochloric acid. The solution was clouded with diethyl ether and the resulting crystalline title product was recovered by filtration in 72% yield as a colorless solid, m.p. 214°–215° C.

Analysis for $C_{17}H_{18}N_2O.HCl$: Calculated: C, 67.43; H, 6.32; N, 9.25; Found: C, 67.38; H, 6.13; N, 9.14.

EXAMPLES 8–12

The following products were prepared from the corresponding intermediates of Examples 2–6 according to the procedure of Example 7.

8. 4-Amino-N-(2,3-dihydro-1H-inden-1-yl)benzamide, 80% yield, m.p. 166°–168° C.

Analysis for $C_{16}H_{16}N_2O$: Calculated: C, 76.16; H, 6.39; N, 11.10; Found: C, 75.63; H, 5.74; N, 10.20.

9. (S)-4-amino-N-[1-(1-naphthalenyl)ethyl]benzamide hydrochloride, 36% yield, m.p. 217°–219° C.

Analysis for $C_{19}H_{18}N_2O.HCl$: Calculated: C, 69.83; H, 5.86; N, 8.57; Found: C, 70.03; H, 6.01; N, 8.43.

10. 4-Amino-N-(5,6,7,8-tetrahydro-1-naphthalenyl)benzamide, 83% yield, m.p. 173°–175° C.

Analysis for $C_{17}H_{18}N_2O$: Calculated: C, 76.66; H, 6.81; N, 10.52; Found: C, 76.52; H, 6.95; N, 10.27.

11. 4-Amino-N-1-naphthalenylbenzamide hydrochloride, 37% yield, m.p. 210°–211° C.

Analysis for $C_{17}H_{14}N_2O.HCl$: Calculated: C, 68.34; H, 5.06; N, 9.38; Found: C, 68.52; H, 5.29; N, 9.60.

12. 4-Amino-N-2-naphthalenylbenzamide, 81% yield, m.p. 219°–221° C.

Analysis for $C_{17}H_{14}N_2O$: Calculated: C, 77.84; H, 5.38; N, 10.68; Found: C, 77.85; H, 5.66; N, 10.38.

The following formulation examples may employ as active compounds any of the pharmaceutical compounds of the invention or their pharmaceutically acceptable salts.

EXAMPLE 13

Hard gelatin capsules are prepared using the following ingredients:

| | Quantity (mg/capsule) |
|---|---|
| 4-Amino-N—(2,3-dihydro-1H—inden-1-yl)benzamide sulfate | 250 |
| Starch dried | 200 |
| Magnesium stearate | 10 |

The above ingredients are mixed and filled into hard gelatin capsules in 460 mg. quantities.

EXAMPLE 14

A tablet formula is prepared using the ingredients below:

| | Quantity (mg/tablet) |
|---|---|
| 4-Amino-N—(1,2,3,4-tetrahydro-1-naphthalenyl)-benzamide hydrobromide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 15

An aerosol solution is prepared containing the following components:

| | Weight % |
|---|---|
| (R)—4-Amino-N—[1-(1-naphthalenyl)ethyl]-benzamide hydrochloride | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 16

Tablets each containing 60 mg of active ingredient are made up as follows:

| | |
|---|---|
| 4-Amino-N—[(1-naphthalenyl)methyl]benzamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 17

Capsules each containing 80 mg of medicament are made as follows:

| | |
|---|---|
| 4-Amino-N—(1H—inden-1-yl)-benzamide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 18

Suppositories each containing 225 mg of active ingredient are made as follows:

| | |
|---|---|
| 4-Amino-N—(3,4-dihydro-2-naphthalenyl)benzamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 19

Suspensions each containing 50 mg of medicament per 5 ml. dose are made as follows:

| | |
|---|---|
| 4-Amino-N—(1,2-dihydro-1-naphthalenyl)benzamide hydrochloride | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of Formula I are anticonvulsant agents with a high therapeutic ratio and long half-life and are therefore useful in the treatment and prevention of convulsions in mammals. In particular, the compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the electroshock induced convulsion inhibition assay (E.S.), the compound to be tested was dissolved in water (5% —sufficient hydrochloric acid was added for those compounds which were not isolated as a salt in order to effect dissolution) and administered by gavage to each of ten Cox standard strain albino male mice (18-24 g) at the dose level being investigated. Sixty minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results are summarized in Table I.

TABLE I

| Anti-convulsant Activity of compounds of Formula I | |
|---|---|
| Example No. | Electroshock $ED_{50}$ (mg/kg)* |
| 7 | 44.5 |
| 8 | 31.0 |
| 9 | 110.0 |
| 10 | 100.0 |
| 11 | 62.0 |
| 12 | >200 |

*oral dose (gavage)—See text for methodology.

We claim:
1. A compound of the Formula

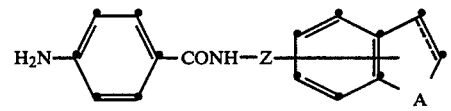

wherein
Z is a bond, —CH$_2$—, or —CHCH$_3$—;
A is —CH$_2$—, or —CH$_2$CH$_2$—; and
--- represents a single or double bond;
and
pharmaceutically acceptable acid addition salts thereof.

2. A compound of claim 1 wherein Z is a bond.
3. A compound of claim 2 wherein the bicyclic system is substituted by the 4-aminobenzamide group on a carbon adjacent to the bridgehead.
4. The compound of claim 3 which is 4-amino-N-(1,2,3,4-tetrahydro-1-naphthalenyl)benzamide or a pharmaceutically acceptable acid addition salt thereof.
5. The compound of claim 3 which is 4-amino-N-(2,3-dihydro-1H-inden-1-yl)benzamide or a pharmaceutically acceptable acid addition salt thereof.
6. A method for treating or preventing convulsions in mammals in need of such treatment which comprises administering to said mammal an effective amount of a compound of claim 1.
7. The method of claim 6 employing the compound 4-amino-N-(1,2,3,4-tetrahydro-1-naphthalenyl)-benzamide or a pharmaceutically acceptable acid addition salt thereof.
8. The method of claim 6 employing the compound 4-amino-N-(2,3-dihydro-1H-inden-1-yl)benzamide or a pharmaceutically acceptable acid addition salt thereof.

9. A pharmaceutical formulation which comprises a compound of claim 1 in association with a pharmaceutically acceptable carrier or diluent.

10. A formulation according to claim 9 employing a compound wherein Z is a bond.

11. A formulation according to claim 10 employing a compound wherein the bicyclic system is substituted by the 4-aminobenzamide group on a carbon atom adjacent to the bridgehead.

12. A formulation according to claim 11 employing 4-amino-N-(1,2,3,4-tetrahydro-1-naphthalenyl)-benzamide or a pharmaceutically acceptable acid addition salt thereof.

13. A formulation according to claim 11 employing 4-amino-N-(2,3-dihydro-1H-inden-1-yl)benzamide or a pharmaceutically acceptable acid addition salt thereof.

* * * * *